(12) United States Patent
Carson et al.

(10) Patent No.: US 7,967,849 B2
(45) Date of Patent: Jun. 28, 2011

(54) ADJUSTABLE MULTI-AXIAL SPINAL COUPLING ASSEMBLIES

(75) Inventors: Robert Carson, Memphis, TN (US); Rodney Ray Ballard, Lakeland, TN (US); James Mirda, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1117 days.

(21) Appl. No.: 11/784,260

(22) Filed: Apr. 6, 2007

(65) Prior Publication Data
US 2008/0249570 A1 Oct. 9, 2008

(51) Int. Cl.
*A61B 17/70* (2006.01)
(52) U.S. Cl. ........ 606/267; 606/265; 606/269; 606/300; 606/305; 606/306
(58) Field of Classification Search .......... 606/264–272, 606/300, 305, 306
See application file for complete search history.

(56) References Cited

U.S. PATENT DOCUMENTS

| | | |
|---|---|---|
| 4,763,644 A | 8/1988 | Webb |
| 4,805,602 A | 2/1989 | Puno |
| 5,207,678 A | 5/1993 | Harms et al. |
| 5,217,497 A | 6/1993 | Mehdian |
| 5,360,431 A | 11/1994 | Puno et al. |
| 5,443,467 A | 8/1995 | Biedermann et al. |
| 5,466,237 A | 11/1995 | Byrd, III et al. |
| 5,474,555 A | 12/1995 | Puno et al. |
| 5,476,464 A | 12/1995 | Metz-Stavenhagen et al. |
| 5,501,684 A | 3/1996 | Schlapfer et al. |
| 5,549,608 A | 8/1996 | Errico et al. |
| 5,554,157 A | 9/1996 | Errico et al. |
| 5,562,661 A | 10/1996 | Yoshimi et al. |
| 5,575,792 A | 11/1996 | Errico et al. |
| 5,586,984 A | 12/1996 | Errico et al. |
| 5,609,593 A | 3/1997 | Errico et al. |
| 5,672,176 A | 9/1997 | Biedermann et al. |
| 5,690,630 A | 11/1997 | Errico et al. |
| 5,716,356 A | 2/1998 | Biedermann et al. |
| 5,728,098 A | 3/1998 | Sherman et al. |
| 5,733,286 A | 3/1998 | Errico et al. |
| 5,817,094 A | 10/1998 | Errico et al. |
| 5,885,286 A | 3/1999 | Sherman et al. |
| 5,891,145 A | 4/1999 | Morrison et al. |
| 5,954,725 A | 9/1999 | Sherman et al. |
| 5,961,517 A | 10/1999 | Biedermann et al. |
| 6,074,391 A | 6/2000 | Metz-Stavenhagen et al. |
| 6,077,262 A | 6/2000 | Schlapfer et al. |
| 6,090,111 A | 7/2000 | Nichols |
| 6,113,601 A * | 9/2000 | Tatar .............................. 606/266 |
| 6,132,432 A | 10/2000 | Richelsoph |
| 6,187,005 B1 | 2/2001 | Brace et al. |
| 6,254,602 B1 | 7/2001 | Justis |
| 6,280,442 B1 * | 8/2001 | Barker et al. ................... 606/60 |

(Continued)

FOREIGN PATENT DOCUMENTS

WO  WO 2005/018471 A1  3/2005

*Primary Examiner* — Eduardo C Robert
*Assistant Examiner* — Ellen C Hammond

(57) ABSTRACT

Coupling assemblies and systems and methods are provided with an anchor member movably coupled with a receiver member extending along a receiver axis. A seat member is movable in the receiver member to assume any one of a plurality of orientations corresponding to an orientation of a connecting element extending through the receiver member transversely to the receiver axis.

22 Claims, 12 Drawing Sheets

U.S. PATENT DOCUMENTS

| | | | |
|---|---|---|---|
| 6,296,642 B1 | 10/2001 | Morrison et al. | |
| 6,443,953 B1 | 9/2002 | Perra et al. | |
| 6,485,491 B1 | 11/2002 | Farris et al. | |
| 6,485,494 B1 | 11/2002 | Haider | |
| 6,520,963 B1 | 2/2003 | McKinley | |
| 6,540,748 B2 | 4/2003 | Lombardo | |
| 6,565,565 B1 | 5/2003 | Yuan et al. | |
| 6,652,526 B1 | 11/2003 | Arafiles | |
| 6,682,532 B2 | 1/2004 | Johnson et al. | |
| 7,022,122 B2 | 4/2006 | Amrein et al. | |
| 7,338,491 B2 * | 3/2008 | Baker et al. | 606/308 |
| 7,618,442 B2 * | 11/2009 | Spitler et al. | 606/266 |
| 2002/0010467 A1 | 1/2002 | Cooper et al. | |
| 2002/0058942 A1 | 5/2002 | Biedermann et al. | |
| 2002/0151900 A1 | 10/2002 | Glascott | |
| 2003/0032957 A1 | 2/2003 | McKinley | |
| 2003/0167058 A1 | 9/2003 | Shluzas | |
| 2003/0216735 A1 | 11/2003 | Altarac et al. | |
| 2004/0181224 A1 | 9/2004 | Biedermann et al. | |
| 2004/0186473 A1 | 9/2004 | Coumoyer et al. | |
| 2005/0261687 A1 * | 11/2005 | Garamszegi et al. | 606/61 |
| 2005/0283157 A1 | 12/2005 | Coates et al. | |
| 2006/0009773 A1 * | 1/2006 | Jackson | 606/73 |
| 2006/0036242 A1 * | 2/2006 | Nilsson et al. | 606/61 |
| 2006/0036244 A1 * | 2/2006 | Spitler et al. | 606/61 |
| 2006/0074419 A1 * | 4/2006 | Taylor et al. | 606/70 |
| 2006/0111713 A1 * | 5/2006 | Jackson | 606/61 |
| 2006/0241599 A1 * | 10/2006 | Konieczynski et al. | 606/61 |
| 2009/0318972 A1 * | 12/2009 | Jackson | 606/264 |

* cited by examiner

ADJUSTABLE MULTI-AXIAL SPINAL COUPLING ASSEMBLIES

BACKGROUND

Spinal implants can be engaged to or along one or more vertebrae of the spinal column for the treatment of various spinal conditions. Fasteners can be provided to secure the implant to a particular location along the spinal column. The implants can be provided to stabilize the spinal column for treatment, either by fixing the spinal column or by permitting at least some motion of the stabilized motion segments.

Coupling assemblies such as multi-axial and uni-axial screws have been employed for securing elongated implants, such as rods or plates, along one or more motion segments of the spinal column. Such screws can comprise many components or parts to secure the implant to the screw that make placement and manipulation of the implant and screw during surgery cumbersome. The interaction between the components of these screws and the elongated implant and the complex spinal anatomy can result in less than optimal orientation and engagement between the components extending along the spinal column. Adjustable coupling assemblies that accommodate the spinal anatomy and the orientation between components and the implants are thus desirable to provide an optimum fit between the components and implant.

SUMMARY

Coupling assemblies and systems and methods are provided with an anchor member coupled with a receiver member extending along a receiver axis. A seat member is movable in the receiver member to assume any one of a plurality of orientations corresponding to an orientation of a connecting element extending through the receiver member arranged transversely to the receiver axis.

According to one aspect, a system for stabilizing a bony segment comprises a connecting element and a coupling assembly engageable to the connecting element. The coupling assembly comprises an anchor member engageable to the bony segment, a receiver member extending proximally from the anchor member along a receiver axis, and a seat member positioned between the connecting element and the anchor member. The receiver member defines a passage for receiving the connecting element along an implantation axis that is transverse to the receiver axis. The seat member includes a proximally oriented support surface for supporting the connecting element so that in the receiver member the seat member is restricted for movement in a plane that includes the implantation axis and the receiver axis. A securing member is engageable to a securing position in the receiver member where the connecting element is secured against the support surface.

According to another aspect, a system for stabilizing a bony segment comprises an elongated connecting element and a coupling assembly engageable to the implant. The coupling assembly comprises an anchor member engageable to the bony segment, a receiver member coupled to and extending proximally from the anchor member along a receiver axis, and a seat member positioned between the connecting element and the anchor member. The receiver member defines a passage for receiving the connecting element along any one of a plurality of implantation axes that are transverse to the receiver axis. The seat member includes a support surface oriented toward the connecting element and opposite engaging surfaces on an outer surface of the seat member. The engaging surfaces are positioned in contact with an adjacent inner surface of the receiver member to prevent the seat member from rotating about the receiver axis while permitting movement of the seat member in the receiver member in a plane that includes the receiver axis and the plurality of implantation axes. The movement of the seat member aligns the support surface with any of the plurality of implantation axes. A securing member is engageable to the receiver member to secure the connecting element in the receiver member.

According to another aspect, a system for stabilizing a bony segment comprises a coupling assembly engageable to the connecting element. The coupling assembly includes an anchor member, a receiver member coupled to and extending proximally from the anchor member, and a seat member positioned in the receiver member. The receiver member includes a pair of arms extending proximally along a receiver axis centrally located between the arms. The arms define a passage for receiving an elongate connecting element along any one of a plurality of implantation axes that are transverse to the receiver axis. The seat member includes a proximally oriented support surface. The seat member is received in movable engagement with the receiver member such that movement of the seat member is limited to a plane including the receiver axis and the plurality of implantation axes to align the support surface along any of the plurality of implantation axes. A securing member is engageable to the receiver member proximally of the anchor member.

According to another aspect, a method for securing a connecting element along a spinal column comprises: engaging an anchor member to a vertebra; positioning the connecting element in a receiver member extending from the anchor member along a receiver axis and with the connecting element extending generally parallel to a sagittal plane of the spinal column and transversely to the receiver axis; contacting the connecting element with a seat member in the receiver member, the seat member being located between the connecting element and the anchor member; moving the seat member generally parallel to the sagittal plane to accommodate a selected angular orientation of the connecting element relative to the receiver axis of the receiver member; and securing the connecting element in the receiver member in the selected angular orientation.

These and other aspects will be discussed further below.

DETAILED DESCRIPTION OF THE ILLUSTRATED EMBODIMENTS

Figure 1:
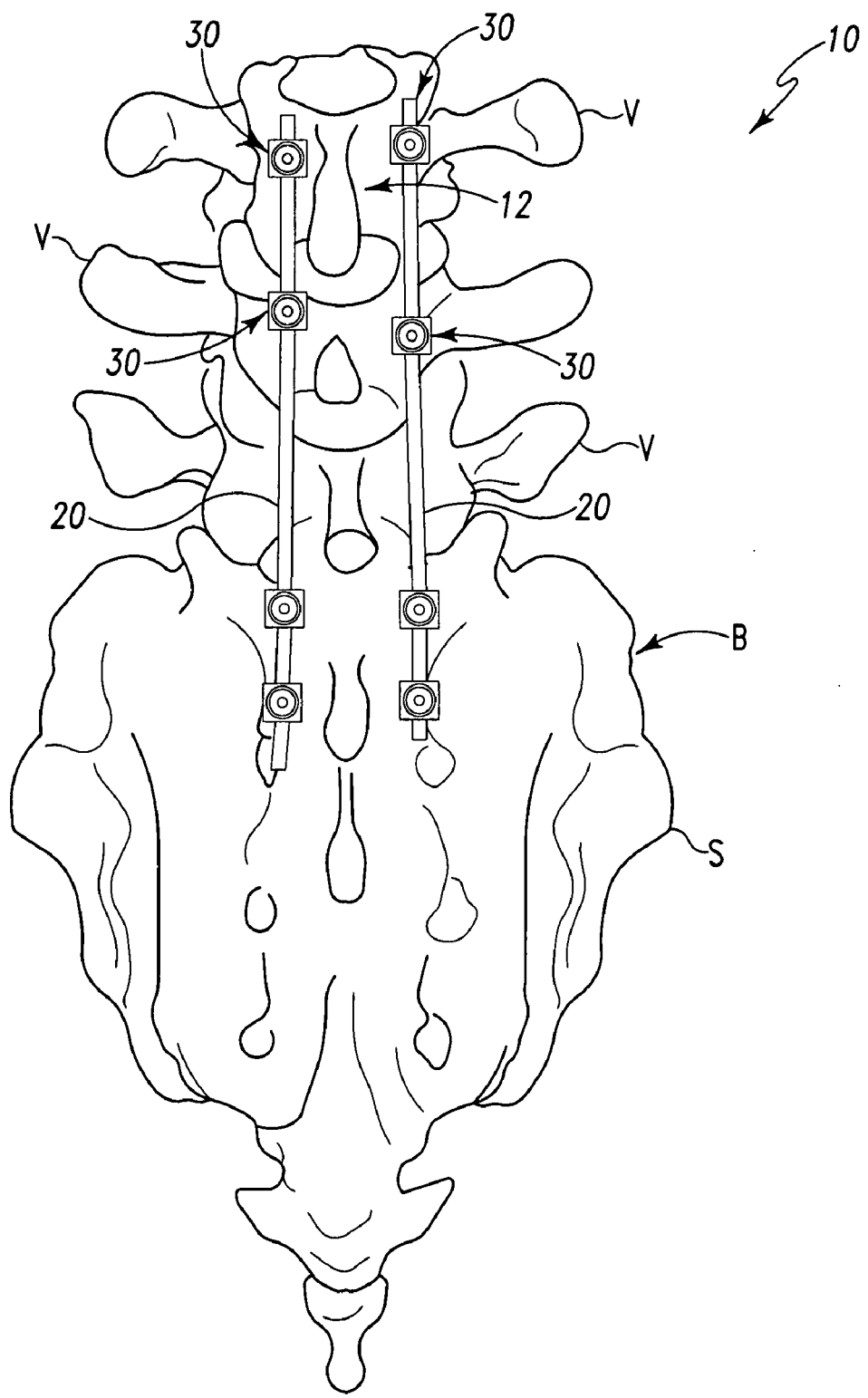
FIG. 1 is a posterior elevation view of a spinal column segment with stabilization systems engaged thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Coupling assemblies are provided to secure one or more elongated connecting elements along the spinal column while providing sagittal angle adjustment capabilities between the implant and the coupling assembly. The coupling assemblies each include an anchor member for engaging the coupling assembly to an underlying bony structure and a receiver member for receiving the connecting element and to which the anchor member is movably coupled. A securing member secures the connecting element to the receiver member. The coupling assemblies also include a seat member in the receiver member, and the connecting element is secured between the seat member and the securing member. The seat member is structured to contact the connecting element and is movable in the receiver member in a plane that includes the axis along which the connecting element extends and an axis along which the receiver member extends. The movement of the seat member allows a support surface of the seat member to be oriented to contact the connecting element along a length of the support surface even when the connecting element is non-orthogonally oriented to the axis of the receiver member. The securing member is positionable to engage the connecting element and secure it against the support surface of the seat member in the receiver member.

FIG. 1 illustrates a posterior spinal implant system 10 located along a spinal column of a patient. More specifically, implant system 10 can be affixed to bones B of the spinal column segment 12 from a posterior approach. Bones B can include the sacrum S and several vertebrae V. Implant system 10 generally includes several coupling assemblies 30 and elongated connecting elements 20 structured to selectively interconnect with coupling assemblies 30. Connecting elements 20 may be a spinal rod, plate, bar, or other elongated element having a length to extend between at least two vertebrae. Connecting element 20 may be solid or hollow along some or all of its length and/or may be of homogenous or heterogeneous composition. In implant system 10, coupling assemblies 30 are affixed to various locations of the spinal column segment 12 and interconnected with connecting elements 20. Spinal implant system 10 may be used for, but is not limited to, treatment of degenerative spondylolisthesis, fracture, dislocation, scoliosis, kyphosis, spinal tumor, and/or a failed previous fusion.

Figures 2, 3:
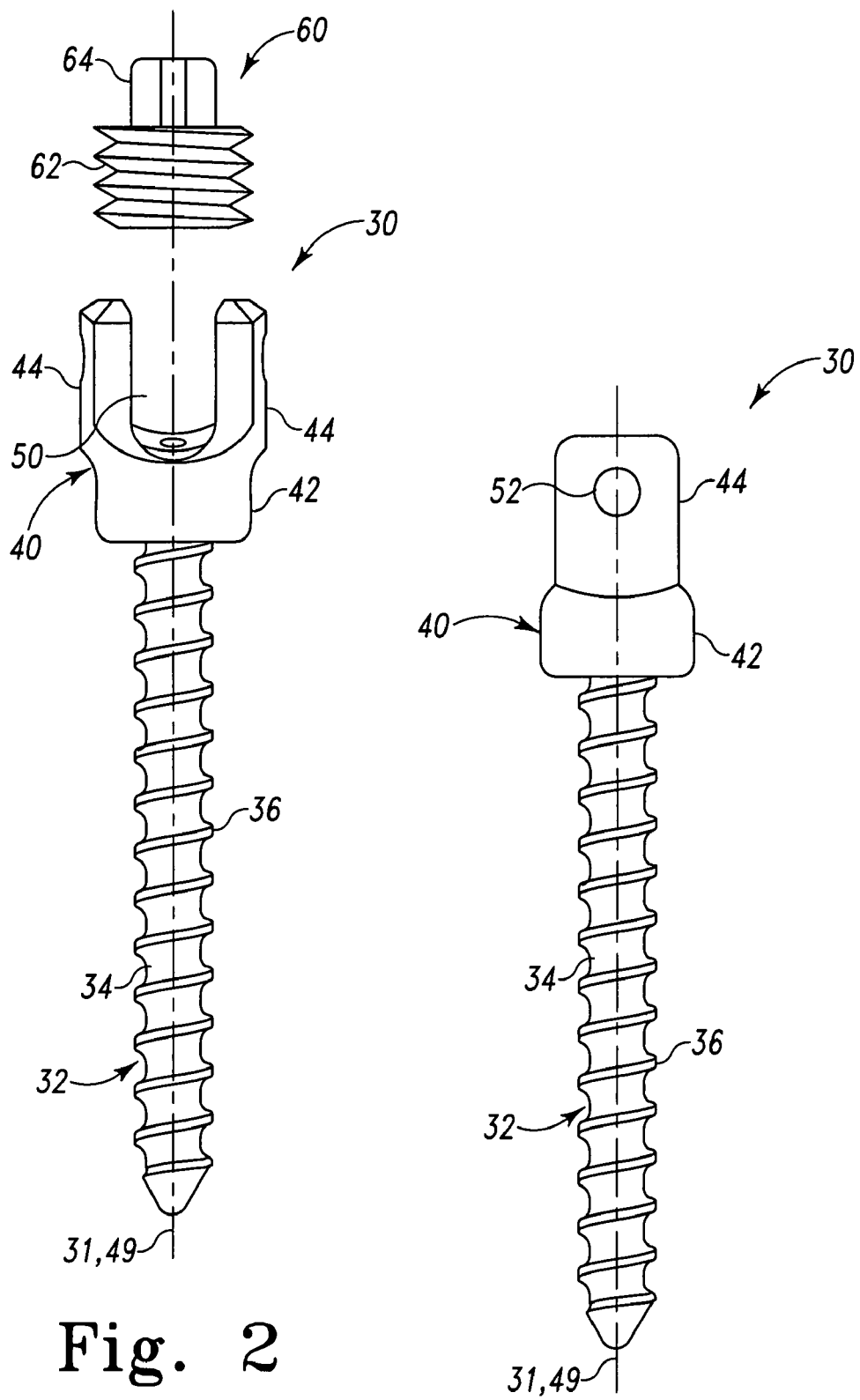
FIG. 2 is an elevation view of a coupling assembly and a securing member in exploded view from the coupling assembly.
FIG. 3 is an elevation view of the coupling assembly of FIG. 2 rotated 90 degrees about its central axis.
Figure 4:
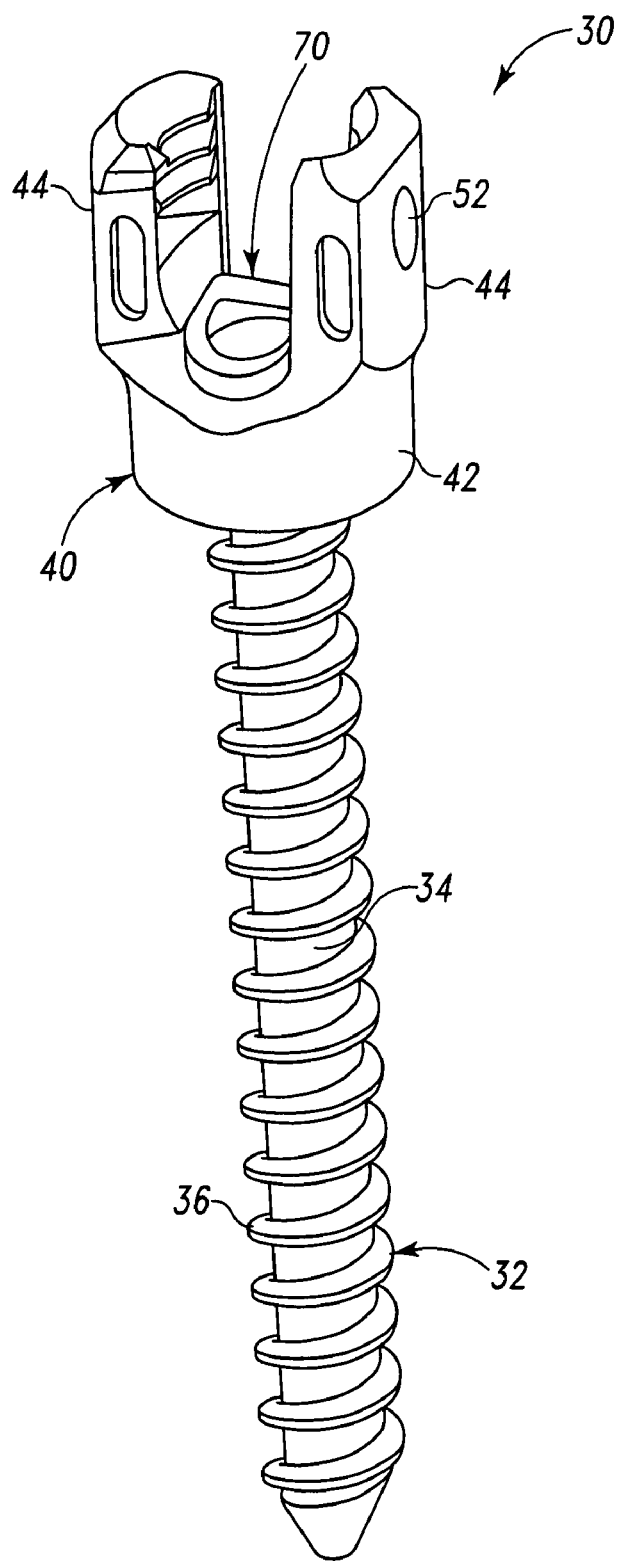
FIG. 4 is a perspective view of the coupling assembly.

Referring to FIGS. 2-4, there is shown a coupling assembly 30 including an anchor member 32, a receiver member 40 coupled to anchor member 32, and a securing member 60. Anchor member 32 and receiver member 40 include a non-pivoted orientation shown in FIGS. 2-4 where receiver axis 49 is aligned along a longitudinal axis 31 of anchor member 32. Receiver member 40 is pivotal relative to anchor member 32 to any one of a number of positions defined by a cone extending proximally from anchor member 32. Anchor member 32 is also similarly pivotal relative to receiver member 40. Other pivoting arrangements between anchor member 32 and receiver member 40 are also contemplated. For example, on one embodiment anchor member 32 is pivotal in a single plane or in a limited number of planes relative to receiver member 40. Non-pivotal and fixed arrangements between anchor member 32 and receiver member 40 are also contemplated.

Connecting element 20 is positionable on, in or about receiver member 40, and securing member 60 is movable relative to connecting element 20 and receiver member 40 to secure connecting element 20 to coupling assembly 30. Coupling assembly 30 includes a seat member 70 between anchor member 32 and connecting element 20 that includes a proximally oriented support surface for contacting and supporting connecting element 20. Connecting element 20 is engaged along one or more vertebrae of the spinal column with one or more coupling assemblies 30 or any other type of fastener in combination with one or more coupling assemblies 30 to provide, for example, a spinal stabilization system.

Anchor member 32 includes an elongated shaft 34 extending along longitudinal axis 31 and enlarged head 38 (FIG. 6) at the proximal end of shaft 34. Elongated shaft 34 includes outer thread profile 36 to threadingly engage the bony structure. Head 38 includes a tool recess 39 to receive a driving tool to facilitate engagement of anchor member 32 to the underlying bone, and ridges along an upper surface of head 38 of anchor member 32 are engaged by seat member 70 to lock the anchor member 32 in position relative to receiver member 40. Various forms for anchor member 32 are contemplated, including threaded and non-threaded anchors, uni-axial and multi-axial arrangements, hooks, clamps, spikes, cables, interbody implants, fusion devices, non-cannulated screws, fenestrated screws, staples, and bolts, for example.

Securing member 60 is movably engageable with receiver member 40 to secure connecting element 20 in engagement with seat member 70. Securing member 60 includes a proximal break-off portion 64 and a distal receiver engaging portion 62, although embodiments without break-off portion 64 are contemplated. Receiver engaging portion 62 is illustrated as an externally threaded set screw that engages an internal thread profile along receiver member 40, as discussed further below. Other configurations are also contemplated, including internally threaded securing members positioned around the receiver member, securing members that slide lock into the receiver member, securing members that pivot lock or bayonet lock to the receiver member, and securing members that provide a friction fit with the receiving member, for example.

Figure 15:
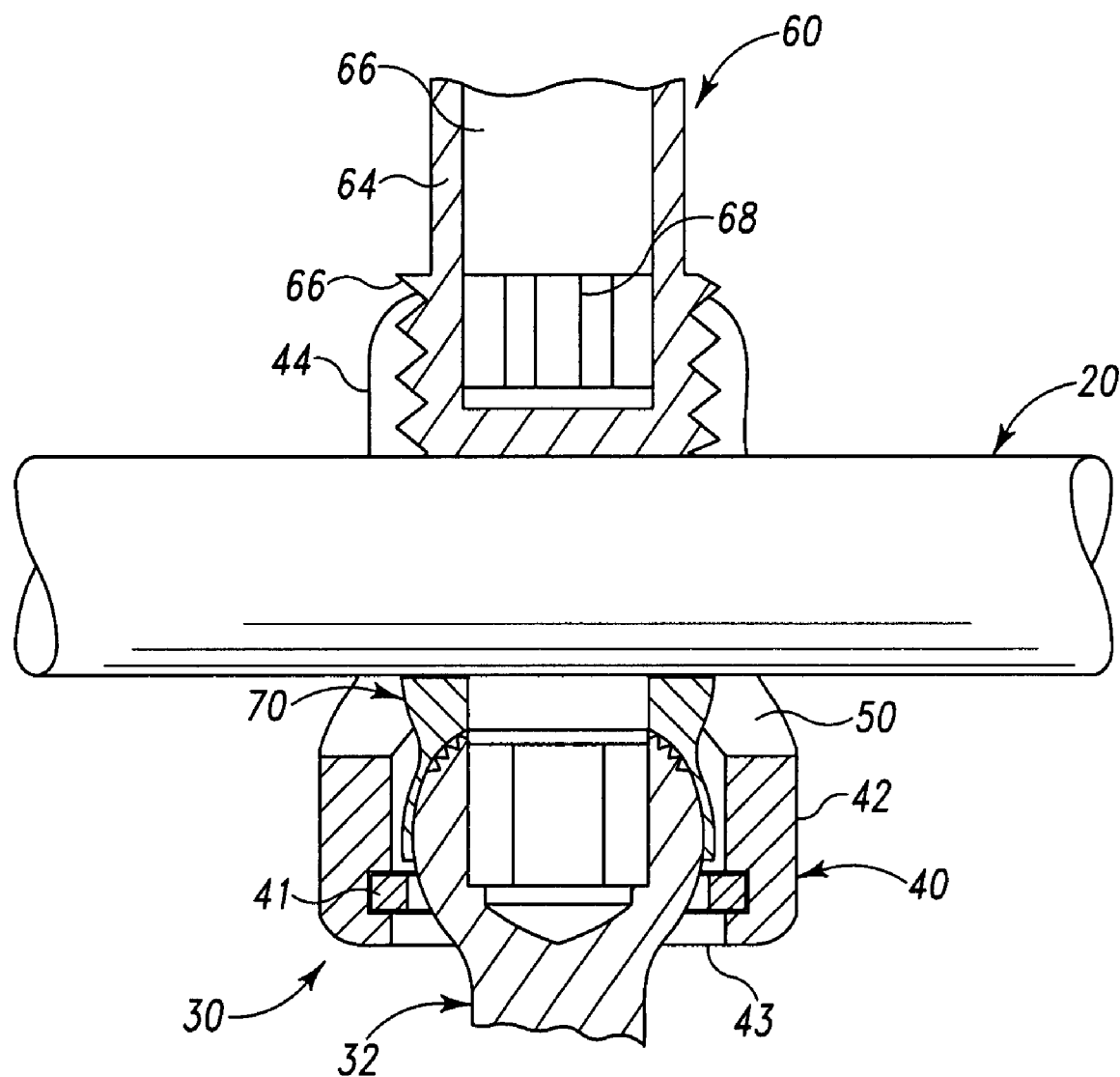
FIG. 15 is a longitudinal section view of a portion of the coupling assembly of FIG. 2 with the connecting element in the receiver member in a first orientation and the securing member engaged to the receiver member.
Figure 16:
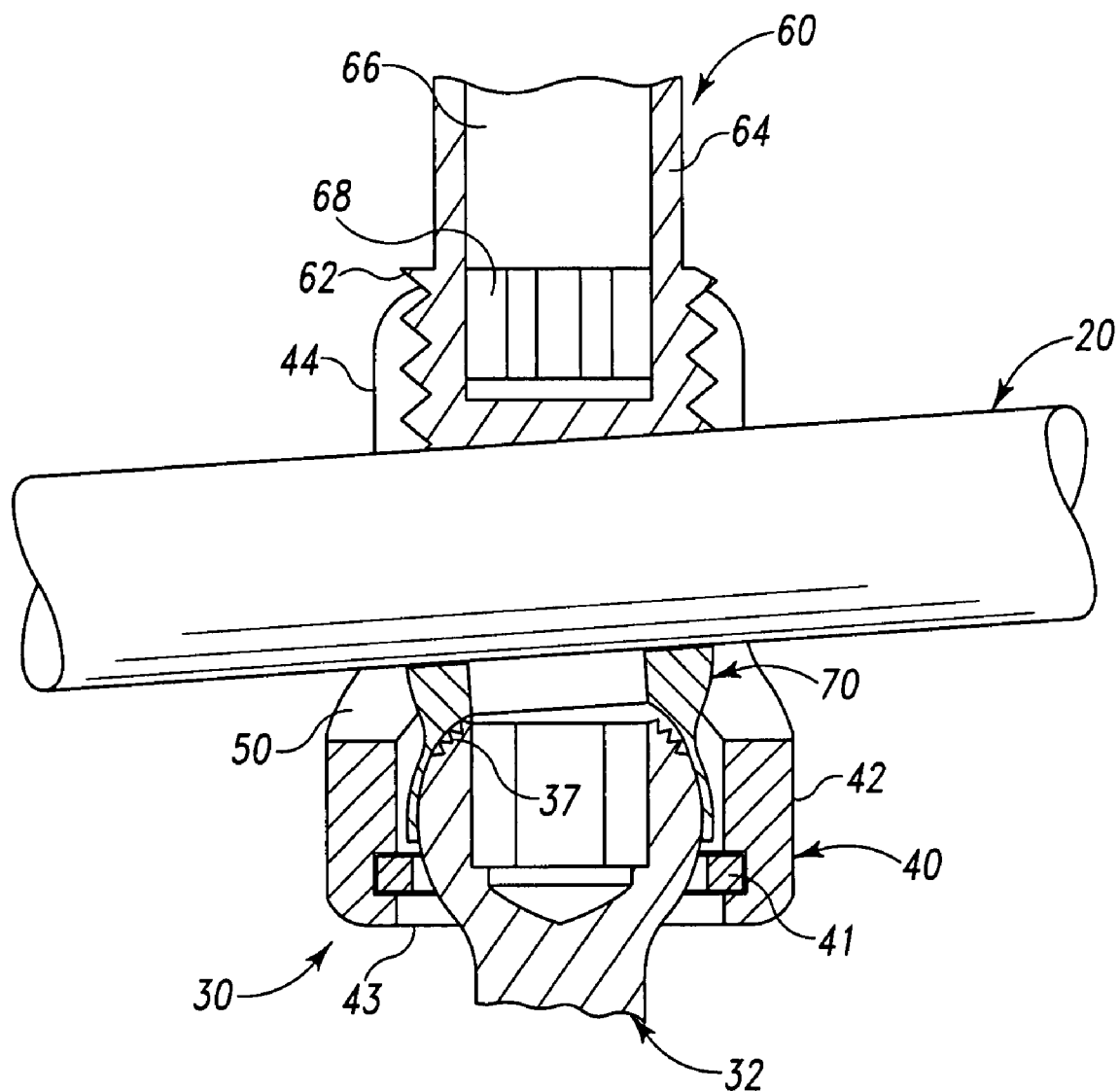
FIG. 16 is a longitudinal section view of a portion of the coupling assembly of FIG. 2 with the connecting element in the receiver member in a second orientation and the securing member engaged to the receiver member.

As further shown in FIGS. 15 and 16, proximally opening first tool recess 66 is formed in break-off portion 64, and a proximally opening second tool recess 68 is formed in receiver engaging portion 62 adjacent to and in communication with first tool recess 66. A driving tool in first tool recess 66 can be manipulated to move securing member 60 relative to receiver member 40 and into engagement with connecting element 20 until sufficient resistance to movement of securing member 60 is encountered to create torque to remove break-off portion 64. Second tool recess 68 is accessible to allow a tool to be positioned therein to apply force to tighten or loosen securing member 60 even when break-off portion 64 is removed.

Figure 18:
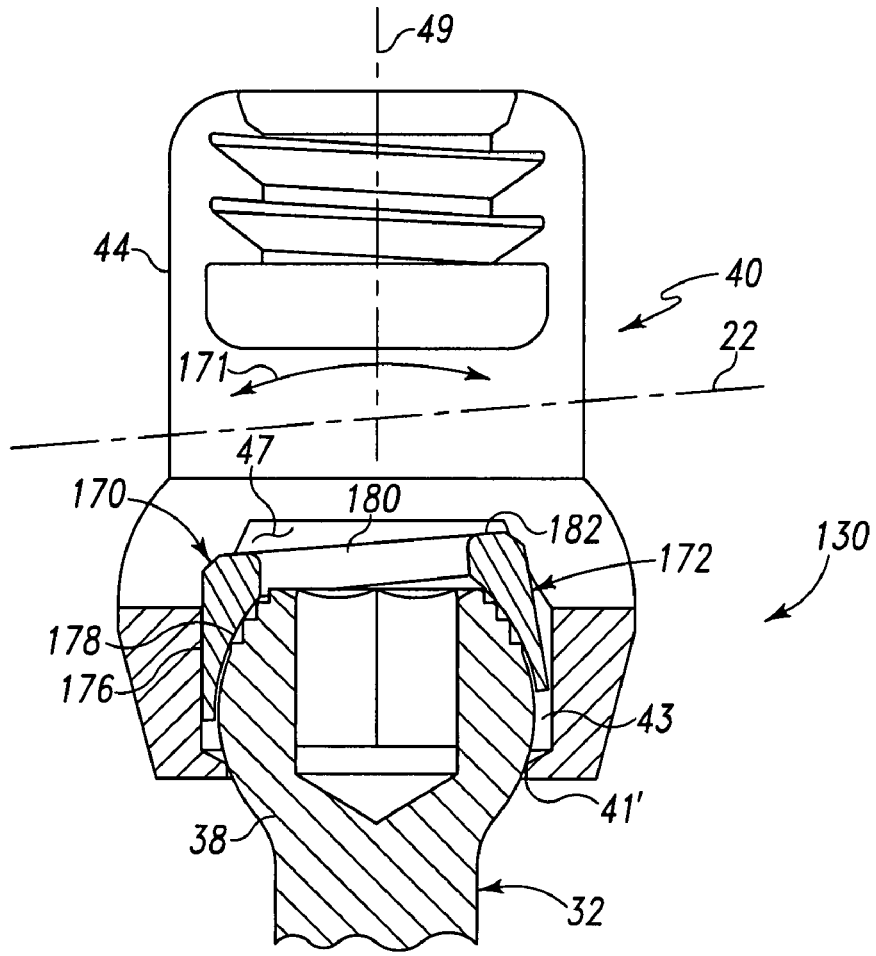
FIG. 18 is a longitudinal sectional view showing the seat member of FIG. 17 positioned in the receiver member and in an angular orientation to the anchor member.
Figure 19:
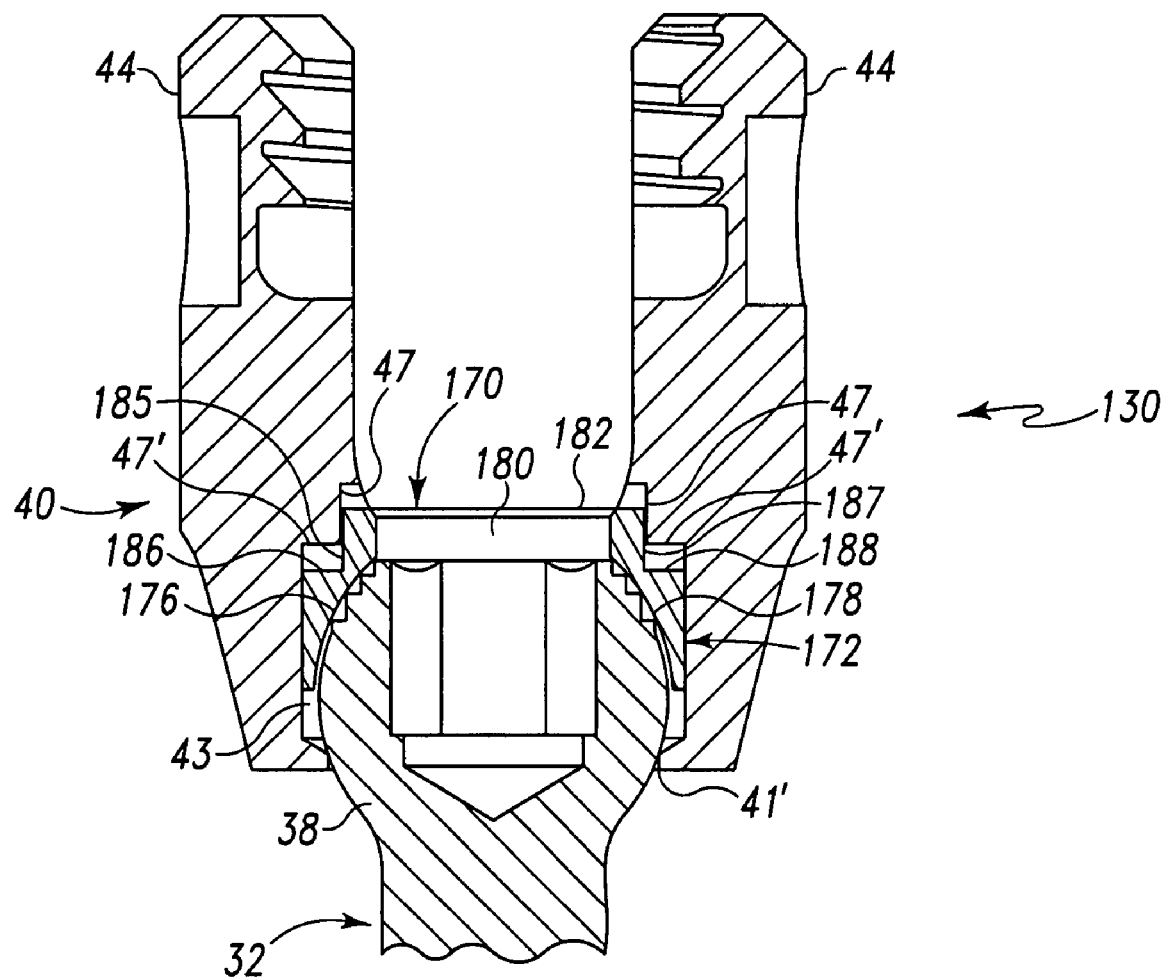
FIG. 19 is a sectional view of the coupling assembly of FIG. 18 looking in a direction that is orthogonal to the direction of the section view of FIG. 18.

Receiver member 40 includes a lower or distal portion 42 that forms a distally opening receptacle 43 to receive a head 38 of anchor member 32 therein. Head 38 of anchor member 32 is pivotally captured and retained in receiver member 40 with a retaining member 41. Retaining member 41 is in the form of a C-shaped ring with a central opening through which shaft 34 of anchor member 32 is positioned. The underside of head 38 is supported on retaining member 41 when receiver member 40 is fully proximally extended from anchor member 32. Other means for securing anchor member 32 in receiver member 40 are also contemplated. For example, FIGS. 18 and 19 show receiving member 40 that forms the lower opening of receiver member 40 with a reduced size to retain head 38 with an integral lip 41' extending around receptacle 43. Other embodiments contemplate providing retaining structures such as collars, washers, bushings, or other devices around receiver member 40 and anchor member 32.

A pair of arms 44 extends axially and proximally from opposite sides of lower portion 42 to form a receiving portion or passage 50 to receive connecting element 20 and engage securing member 60. Receptacle 43 opens proximally between arms 44. Connecting element 20 extends between arms 44 so that it is oriented to lie in a plane that bifurcates arms 44, and connecting element 20 extends in one or both directions from the arms 44 along an implantation axis at the implantation site. In FIG. 1, connecting element 20 extends along an implantation axis that is parallel or generally parallel to the sagittal plane of the spinal column. To accommodate the anatomy of the spinal column, the implantation axis lies parallel or generally parallel to the sagittal plane and in any one of a plurality of orientations relative to the coronal plane, including extending parallel to the coronal plane and extending obliquely to the coronal plane.

Arms 44 each include an inner surface 47 extending from receptacle 43 to internal thread profile 46. Internal thread profile 46 extends to the proximal end of arms 44, and is configured to threadingly engage securing member 60. Opposing arms 44 define receiving portion or passage 50 therebetween that is sized to receive connecting element 20 proximally of seat member 70. Arms 44 also each include an outer recess 52 to receive and facilitate engagement by and manipulation with insertion and/or reduction instrumentation (not shown.)

Receiver member 40 further includes seat member 70 positioned between arms 44 adjacent head 38 of anchor member 32. Seat member 70 is located adjacent receptacle 43 and distally of thread profile 46. In one embodiment, seat member 70 includes a distally oriented socket portion 72 that receives head 38 while permitting movement of seat member 70 about head 38. Seat member 70 also includes a proximally oriented saddle portion 74 that contacts connecting element 20.

Figure 5:
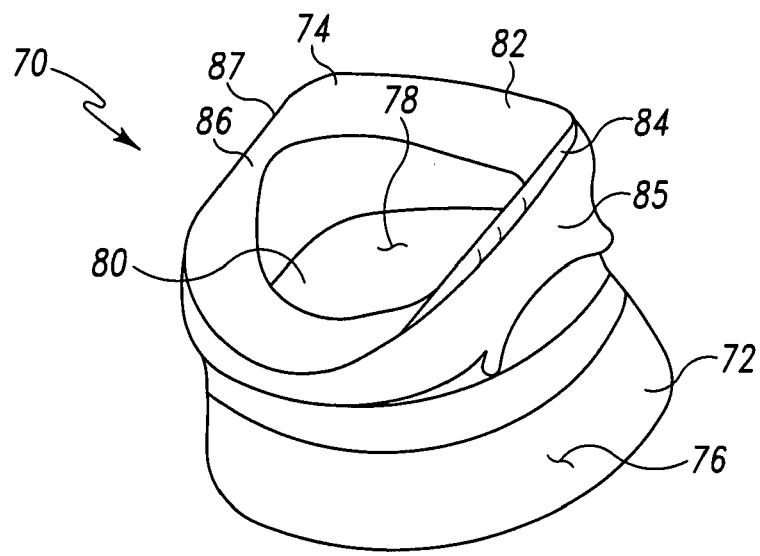
FIG. 5 is a perspective view of a seat member of the coupling assembly of FIG. 2.

Seat member 70 is shown in isolation in FIG. 5, and in section view when assembled with coupling assembly 30 as shown in FIGS. 6-16. Socket portion 72 includes a spherical shape with an outer convex surface 76 and an inner concave surface 78. Inner concave surface 78 forms a recess to receive head 38, and outer convex surface 76 resides in receptacle 43 and is sized and shaped relative to receptacle 43 so that seat member 70 is movable in receptacle 43.

Figure 8:
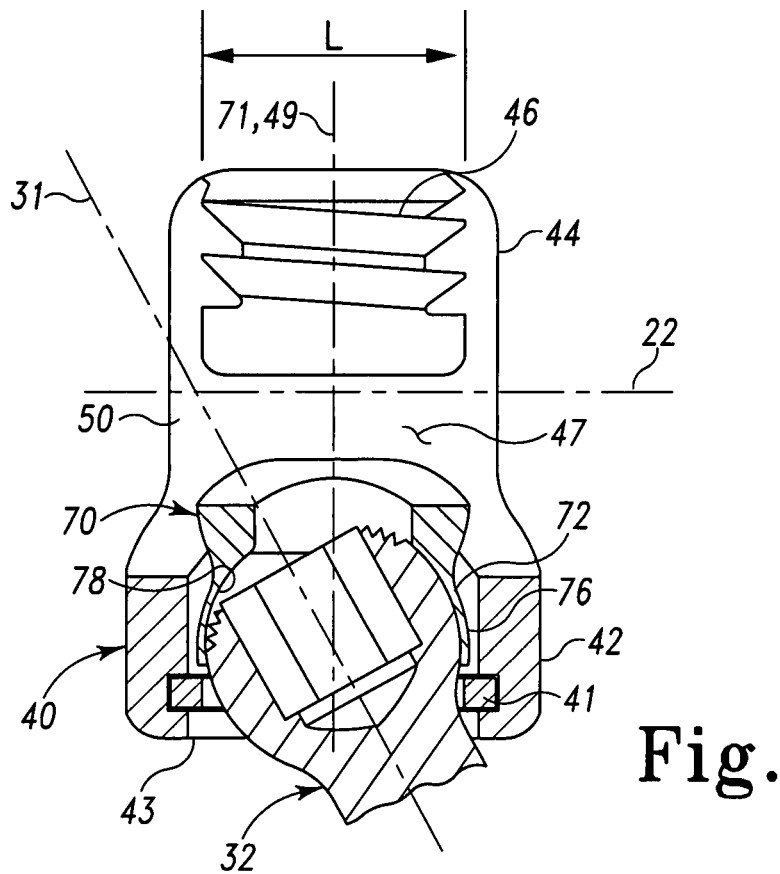
FIG. 8 is a longitudinal section view of a portion of the coupling assembly of FIG. 2 showing another orientation of the components of the coupling assembly.

Seat member 70 includes a through-hole 80 that extends to and opens through saddle portion 74 and socket portion 72. Through-hole 80 of seat member 70 is in communication with head 38 of anchor member 32 to receive a driving tool (not shown) to apply a driving force to anchor member 32. Saddle portion 74 includes a concavely curved proximal support surface 82 extending around through-hole 80. Saddle portion 74 includes proximally extending ears 84, 86 on opposite sides thereof that project proximally and form convexly rounded edges around saddle portion 74. Support surface 82 is concavely curved in the direction extending from ear 84 to ear 86. In the direction transverse to the direction between ears 84, 86, which corresponds to the direction of the implantation axis of the connecting element, support surface 82 has a linear profile along length L (FIG. 8.) The concave and linear profiles conform to the profile of the outer surface of connecting element 20 to provide an intimate surface-to-surface fit therewith and fully support the connecting element 20 on seat member 70 along length L of support surface 82.

Seat member 70 also includes outer engaging surfaces 85, 87 along ears 84, 86, respectively, that contact inner surface 47 of the adjacent arm 44 to orient and maintain the orientation of seat member 70 in receiver member 40. Engaging surfaces 85, 87 permit articulating movement of the seat member 70 in receiver member 40 in a uni-planar or substantially uni-planar direction in a plane that includes the implantation axis of the connecting element while preventing rotation of seat member 70 about receiver axis 49. In the illustrated embodiment, engaging surfaces 85, 87 are flats or flat surface portions. Other embodiments contemplate other surface configurations to orient seat member 70 in receiver member and prevent rotation about the receiver axis. Accordingly, when implanted in the FIG. 1 configuration, connecting element 20 extends along an implantation axis which is parallel or generally parallel to the sagittal plane of the spinal column, and seat member 70 can articulate in a direction parallel or generally parallel to the sagittal plane of the spinal column to accommodate the angular orientation of connecting element 20 through receiver member 40.

Figure 6:
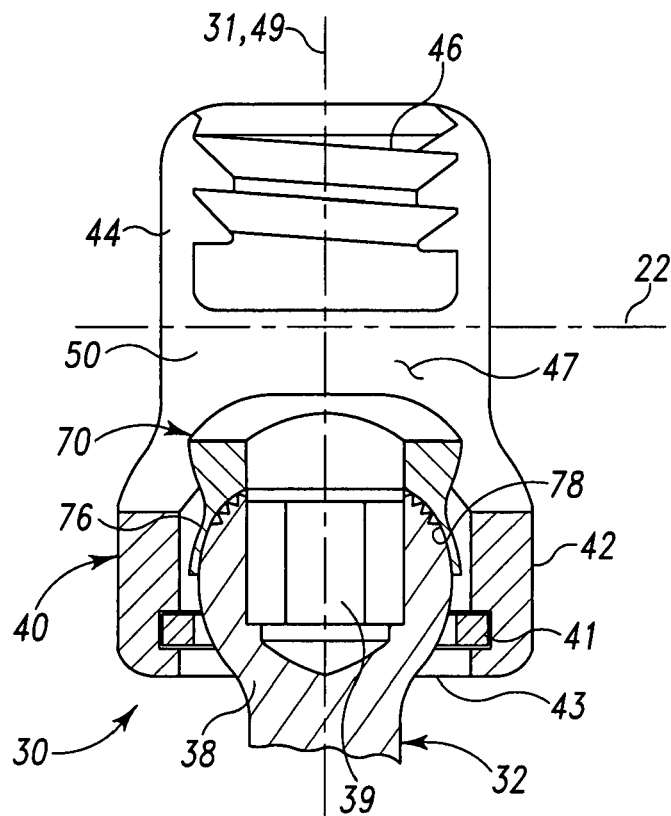
FIG. 6 is a longitudinal section view of a portion of the coupling assembly of FIG. 2 showing one orientation of the components of the coupling assembly.
Figure 7:
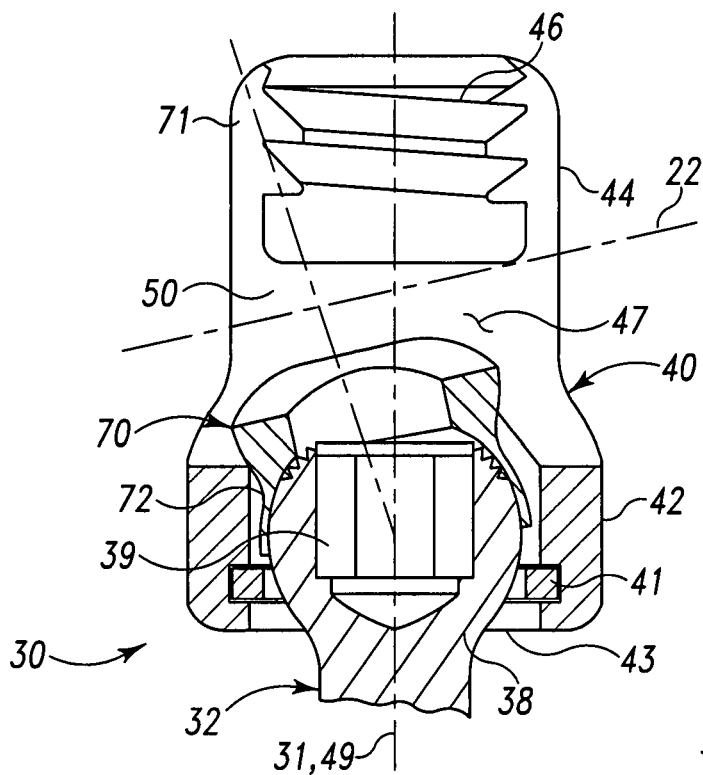
FIG. 7 is a longitudinal section view of a portion of the coupling assembly of FIG. 2 showing another orientation of the components of the coupling assembly.

Various orientations of the components of coupling assembly 30 are possible to permit the coupling assembly to be engaged to and fully support the connecting element 20 even when the implantation axis is non-orthogonal to receiver axis 49. In FIGS. 6-10, head 38 of anchor member 32 is seated against retaining member 41 since receiver member 40 is fully extended proximally relative to anchor member 32. In FIG. 6, the components of coupling assembly 30 are aligned so that the orientation of seat member axis 71 of seat member 70 and the receiver axis 49 of receiver member 40 are aligned with longitudinal axis 31 of anchor member 32. In this orientation, seat member 70 supports connecting element 20 along an implantation axis 22 that extends orthogonally to longitudinal axis 31 and receiver axis 49. In FIG. 7, seat member 70 has been articulated or moved so that support surface 82 extends along an implantation axis 22 that is non-orthogonal or obliquely oriented to longitudinal axis 31 and the receiver axis 49 of receiver member 40. Seat member 70 is oriented so that seat member axis 71 is orthogonal to implantation axis 22 and support surface 82 extends generally parallel or parallel to implantation axis 22.

In FIG. 8, anchor member 32 is oriented so that longitudinal axis 31 is oriented obliquely to receiver axis 49. Implantation axis 22 is orthogonal to receiver axis 49, and seat member axis 71 is aligned with receiver axis 49 so that support surface 82 extends parallel or generally parallel to implantation axis 22. Connecting element 20 is fully supported along length L of support surface 82 when positioned in receiver member 40 along implantation axis 22.

Figure 9:
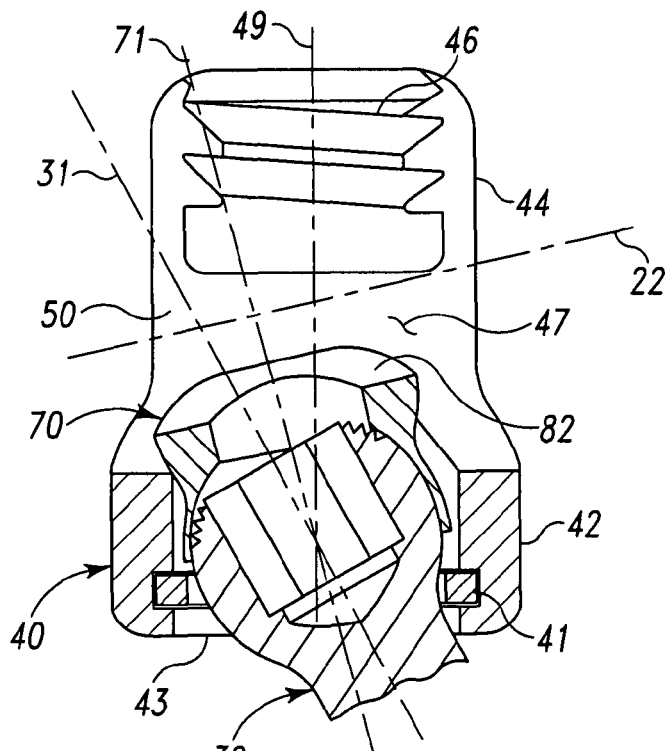
FIG. 9 is a longitudinal section view of a portion of the coupling assembly of FIG. 2 showing another orientation of the components of the coupling assembly.

In FIG. 9, seat member 70 has been articulated or moved so that seat member axis 71 extends between longitudinal axis 31 and receiver axis 49 and is obliquely oriented to the axes 31, 49. Implantation axis 22 is also obliquely oriented to both receiver axis 49 and longitudinal axis 31, and implantation axis 22 is orthogonally oriented to seat member axis 71. When connecting element 20 is positioned in receiver member 40 along implantation axis 22, support surface 82 extends parallel or generally parallel to connecting element 20 and fully supports connecting element 20 along length L.

Figure 10:
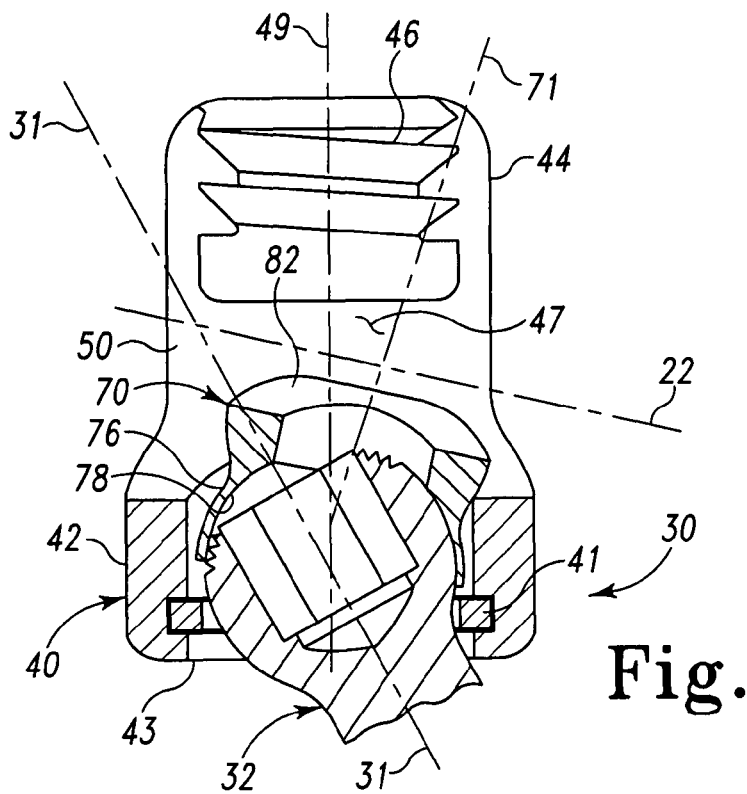
FIG. 10 is a longitudinal section view of a portion of the coupling assembly of FIG. 2 showing another orientation of the components of the coupling assembly.

In FIG. 10, seat member 70 has been moved or articulated in a direction opposite that of FIG. 9 so that receiver axis 49 is located between longitudinal axis 31 and seat member axis 71. Implantation axis 22 is obliquely oriented to receiver axis 49, and seat member axis 71 is orthogonally oriented to implantation axis 22. The connecting element 20 is thus secured in the coupling assembly 30 along implantation axis 22 so that it slopes proximally in receiver member 40 from right to left, whereas in FIG. 9 connecting element 22 is secured in coupling assembly 30 so that it slopes distally relative to receiver member 40 from right to left. In either arrangement, support surface 82 is arranged parallel or generally parallel to connecting element 20 so that connecting element 20 is fully supported along length L of support surface 82.

In FIGS. 11-14, anchor member 32 includes head 38 spaced proximally from retaining member 41 since receiver member 40 is displaced distally along anchor member 32. Seat member 70 contacts the inner wall surface 47 in receptacle 43 with socket portion 72 to maintain head 38 within receptacle 43. The convexly curved outer surface of socket portion 72 permits pivoting movement of seat member 70 relative to receiver member 40.

Figure 11:
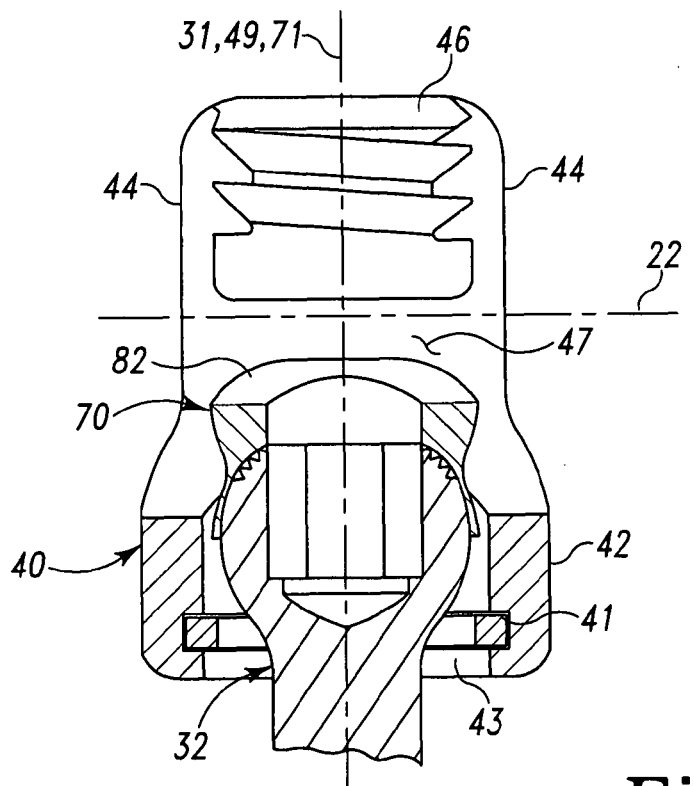
FIG. 11 is a longitudinal section view of a portion of the coupling assembly of FIG. 2 showing another orientation of the components of the coupling assembly.
Figure 12:
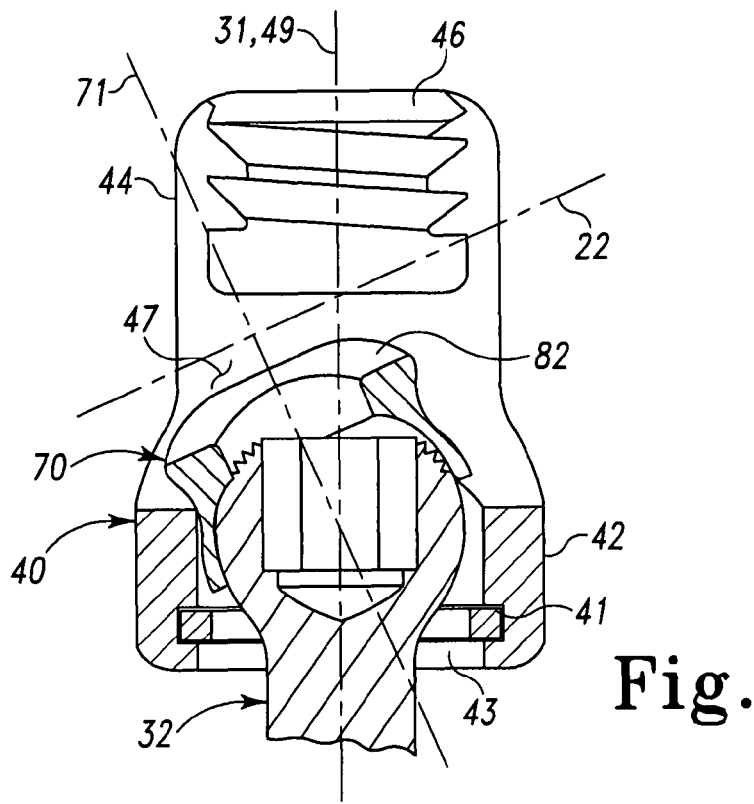
FIG. 12 is a longitudinal section view of a portion of the coupling assembly of FIG. 2 showing another orientation of the components of the coupling assembly.

In FIG. 11, receiver axis 49 and seat member axis 71 are aligned along longitudinal axis 31 of anchor member 32. Implantation axis 22 extends orthogonally to axes 31, 49 and 71. In FIG. 12, seat member 70 has been moved in receiver member 40 and relative to anchor member 32 so that seat member axis 71 is oblique to receiver axis 49 and longitudinal axis 31. Connecting element 20 can be implanted along implantation axis 22 that is non-orthogonally oriented to axes 31, 49 while seat member 70 is articulates so that support surface 82 is aligned along and parallel or generally parallel to implantation axis 22 to fully support connecting element 20 along length L of support surface 82 of seat member 70.

Figure 13:
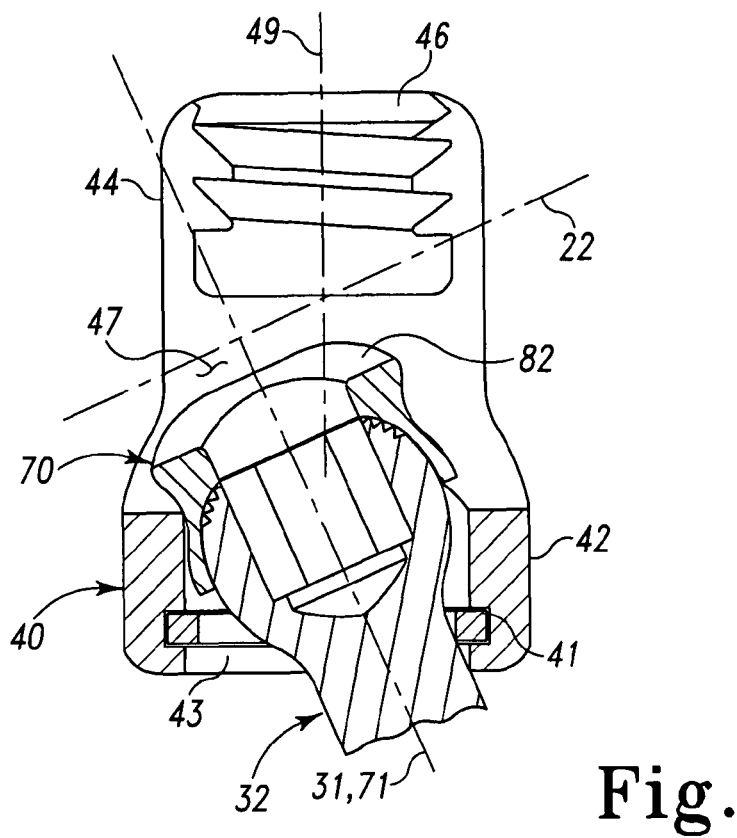
FIG. 13 is a longitudinal section view of a portion of the coupling assembly of FIG. 2 showing another orientation of the components of the coupling assembly.
Figure 14:
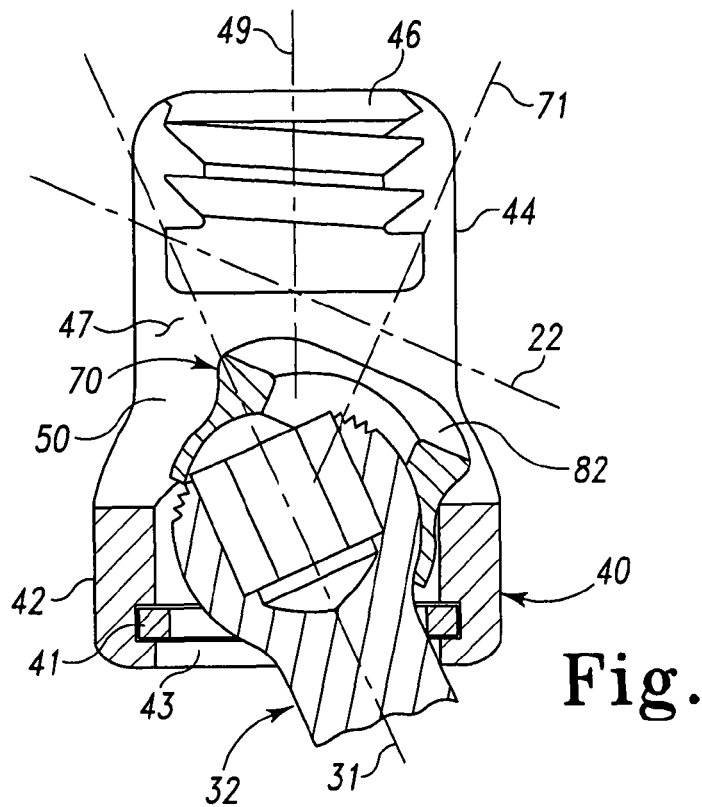
FIG. 14 is a longitudinal section view of a portion of the coupling assembly of FIG. 2 showing another orientation of the components of the coupling assembly.

In FIG. 13 anchor member 32 is pivoted so that longitudinal axis 31 is aligned with seat member axis 71. Receiver axis 49 is obliquely oriented to axes 31, 71, and implantation axis 22 extends non-orthogonally to receiver axis 49. Support surface 82 extends parallel or generally parallel to implantation axis 22 so that connecting element 20 is fully supported along length L of support surface 82. In FIG. 14 anchor member 32 is pivoted so that longitudinal axis 31 is oblique to receiver axis 49, and seat member 70 is articulated or moved so that seat member axis 71 is obliquely oriented to both longitudinal axis 31 and receiver axis 49. Implantation axis 22 extends non-orthogonally to receiver axis 49 and longitudinal axis 31. Support surface 82 extends parallel or generally parallel to implantation axis 22 so that connecting element 20 is fully supported along length L of support surface 82.

Referring to FIGS. 15 and 16, in use anchor member 32 is engaged to an underlying bony structure with receiver member 40 positioned to receive connecting element 20. Connecting element 20 is positioned in passage 50 of receiver member 40 along or adjacent support surface 82 of seat member 70. In the illustrated embodiment, passage 50 forms a U-shaped extending along implantation axis 22. Seat member 70 can be moved relative to anchor member 32 and/or receiver member 40 to orient support surface 82 in the desired alignment with connecting element 20 in receiver member 40, such as shown in FIG. 16, so that support surface 82 is in full contact with connecting element 20 along length L even if implantation axis 22 is non-orthogonal to receiver axis 49.

Securing member 60 is engaged to receiver member 40, and advanced along the internal threads 46 of arms 44 until securing member 60 contacts connecting element 20. In this configuration, connecting element 20 is seated against support surface 82. As securing member 60 is further advanced distally in receiver member 40, socket portion 72 of seat member 70 presses against head portion 38 of anchor member 32. Head portion 38 can include teeth or ridges 37 on the proximal side thereof that bite into or frictionally engage seat member 70 to maintain the relative positioning of the components of the coupling assembly 30 in a fixed condition. Securing member 60 can be advanced in contact with connecting element 20 while receiver engaging portion 62 is threadingly engaged with receiver member 40 until sufficient resistance is encountered to sever break-off portion 64.

In one embodiment, securing member 60 is positioned to rigidly fix connecting element 20, seat member 70, anchor member 32 and receiving member 40 together. Other embodiments contemplate that one or more of anchor member 32, receiver member 40, and seat member 70 is secured in a variable angle or semi-rigid arrangement relative the other components even when securing member 60 and seat member 70 are firmly engaged to connecting element 20. The surface areas of support surface 82 and securing member 60 contact connecting element 20 to provide a desired frictional or clamping engagement with connecting element 20 to maintain it in position relative to coupling assembly 30 while distributing the clamping forces over the entire area of support surface 82.

Figure 17:
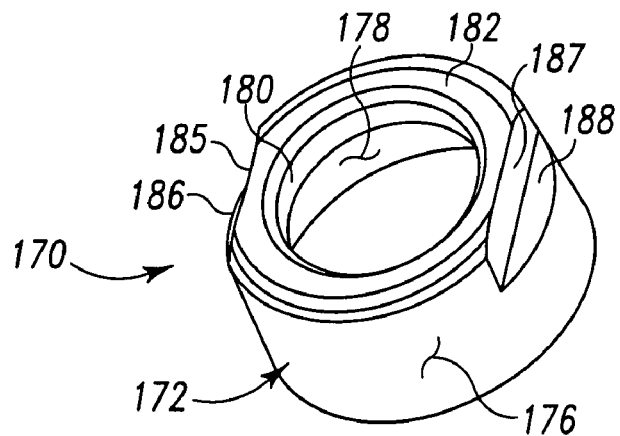
FIG. 17 is a perspective view of another embodiment seat member.

Another embodiment seat member 170 is shown in isolation in FIG. 17, and in section view when assembled with coupling assembly 130 as shown in FIGS. 18-19. Seat member 170 includes a distal socket portion 172 that has a cylindrical shape with an outer convex surface 176 and an inner concave surface 178. Inner concave surface 178 forms a spherical recess to receive head 38 of anchor member 32, and outer convex surface 176 resides in receptacle 43 of receiver member 40 and is sized and shaped relative to receptacle 43 so that seat member 170 is movable in receptacle 43. Seat member 170 also includes a proximal support surface 182 on the proximal side thereof. In the illustrated embodiment, support surface 182 is planar to provide a flat support surface against which connecting element 20 is positioned. Other embodiments contemplate other configurations for support surface 182. For example, the support surface can be of any shape to conform or match a shape of the connecting element to provide a closely matching geometry or other geometry as desired.

Seat member 170 includes a through-hole 180 that extends to and opens through support surface 182 and socket portion 172. Through-hole 180 of seat member 170 is in communication with head 38 of anchor member 32 to receive a driving tool (not shown) to apply a driving force to anchor member 32. Proximal support surface 182 extends around through-hole 80. Socket portion 172 also includes outer engaging surfaces 185, 187 that form an L-shaped indentation along the sides of seat member 70. Engaging surfaces 185, 187 extend proximally from a distal ledge 186, 188 to support surface 182.

As shown in FIG. 19, engaging surfaces 185, 187 contact inner surface 47 of the adjacent arm 44 to orient and maintain the orientation of seat member 170 in receiver member 40. Ledges 186, 188 contact the adjacent distally oriented lip 47' to limit proximal displacement of seat member 70 in receiver member 40. Engaging surfaces 185, 187 permit articulating movement of the seat member 170 in receiver member 40 in a uni-planar or substantially uni-planar direction in a plane that includes the implantation axis 22 of the connecting element 20 and receiver axis 49 while preventing rotation of seat member 170 about receiver axis 49. In the illustrated embodiment, engaging surfaces 185, 187 are flats or flat surface portions. Other embodiments contemplate other surface configurations to orient seat member 170 in receiver member and prevent rotation about the receiver axis 49. Accordingly, when implanted in the FIG. 1 configuration, connecting element 20 extends along implantation axis 22, and seat member 170 can articulate in a direction parallel or generally parallel to the plane including receiver axis 49 and implantation axis 22, as indicated by arrow 171 in FIG. 18, to accommodate the angular orientation of connecting element 20 through receiver member 40.

Connecting element 20 can be structured either alone or in combination with one or more other implants and/or coupling assemblies to provide a desired stabilization effect. In the illustrated embodiment, connecting element 20 is an elongated spinal rod structured to extend between at least two coupling assemblies 30 to stabilize a motion segment between the at least two coupling assemblies. Various forms for connecting element 20 are contemplated, including rods, tethers, cables, wires, plates, and staples, for example. In one specific embodiment, connecting element 20 is a spinal rod comprised of any one or combination of titanium, stainless steel, plastic, polymer, tissue, fabric, or mesh material. Other embodiments contemplate that connecting element 20 can be made from any suitable biocompatible material. Connecting element 20 can have a length adapted to extend along multiple vertebral levels or a single vertebral level. Connecting element 20 can also include a linear profile along its length or a curved profile along its length.

In spinal surgical procedures, connecting element 20 and one or more coupling assemblies 30 and/or other fasteners secure connecting element 20 to the spinal column and are employed unilaterally along one side of the spinal column. Alternatively, a second connecting element 20 and additional coupling assemblies 30, 130 and/or other fasteners are secured to the other side of the vertebral level or levels to be stabilized for bi-lateral stabilization. Multiple connecting elements 20 and corresponding coupling assemblies 30, 130 and/or other fasteners can be secured along the same side of the spinal column in either uni-lateral or bi-lateral stabilization procedures.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The coupling assemblies and connecting elements can be positioned along the spinal column in invasive procedures where skin and tissue are dissected and retracted to expose the implantation locations, or in minimally invasive procedures where one or more of the coupling assemblies and connecting elements are guided through at least the tissue or access portals adjacent the column to the desired implantation location.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for stabilizing a bony segment, comprising:
   a connecting element;
   a coupling assembly engageable to said connecting element, wherein said coupling assembly comprises:
      an anchor member engageable to the bony segment;
      a receiver member extending proximally from said anchor member along a receiver axis, said receiver member defining a passage for receiving said connecting element along an implantation axis that is transverse to said receiver axis;
      a seat member positioned between said connecting element and said anchor member, said seat member including a proximal saddle portion including a support surface for supporting said connecting element, wherein in said receiver member said seat member is restricted for movement in a plane that includes said implantation axis and said receiver axis; and
   a securing member engageable to a securing position in said receiver member where said connecting element is secured against said support surface;
   wherein said proximal saddle portion includes opposite proximally projecting ears and opposite, flat engaging surfaces on an outer surface of said saddle portion extending along said ears, said engaging surfaces contacting an inner surface of said receiver member to restrict said seat member to movement in said plane.

2. The system of claim 1, wherein:
   said anchor member includes a screw having a head pivotally captured in said receiver member; and
   said seat member includes a distal socket portion articulatable relative to said head at least when said securing member is not in said securing position.

3. The system of claim 2, wherein said head includes a plurality of ridges to engage and fix said seat member to said anchor member when said securing member is in said securing position.

4. The system of claim 1, wherein said connecting element is an elongate spinal rod and said receiver member includes a lower portion for pivotally receiving said anchor member, said receiver member further including a pair of arms extending from said lower portion, said pair of arms defining said passage for receiving said spinal rod between said pair of arms.

5. The system of claim 1, wherein said securing member includes a receiver engaging portion threadingly engageable with said receiver member and a proximal break-off portion removable from said receiver engaging portion upon application of a threshold torque to said break-off portion.

6. The system of claim 5, wherein:
said receiver member includes a pair of arms on opposite sides of said passage extending along said receiver axis, wherein said arms are internally threaded; and
said receiver engaging portion includes an externally threaded body engageable to said internally threaded arms.

7. The system of claim 1, wherein said support surface of said seat member is concavely curved in a direction transverse to said implantation axis and linear in a direction along said implantation axis.

8. The system of claim 1, wherein said seat member includes:
a distally opening socket portion configured to pivotally receive said anchor member in said receiver member.

9. The system of claim 8, wherein said seat member includes a through-hole extending through said support surface and into said socket portion.

10. The system of claim 8, wherein said socket portion includes a concavely curved inner surface and a convexly curved outer surface extending around said socket portion.

11. The system of claim 1, wherein:
said anchor member includes a screw with an enlarged head received in a distal portion of said receiver member and a shaft extending distally from said head through a distally oriented opening of said receiver member; and
said coupling assembly includes a retaining member engaged to said receiver member around said distally oriented opening and positioned about said shaft adjacent a distal side of said head, said retaining member capturing said screw in said receiver member.

12. The system of claim 1, wherein said support surface of said seat member is flat.

13. A system for stabilizing a bony segment, comprising:
an elongated connecting element;
a coupling assembly engageable to said connecting element, wherein said coupling assembly comprises:
an anchor member engageable to the bony segment;
a receiver member coupled to said anchor member and extending proximally therefrom along a receiver axis, said receiver member defining a passage for receiving said connecting element along any one of a plurality of implantation axes that are transverse to said receiver axis;
a seat member positioned between said connecting element and said anchor member, said seat member including a proximal saddle portion having opposite proximally projecting ears, a support surface oriented toward said connecting element and opposite engaging surfaces on an outer surface thereof, said engaging surfaces having flat surfaces and being positioned in contact with an adjacent inner surface of said receiver member to prevent said seat member from rotating about said receiver axis while permitting movement of said seat member in said receiver member in a plane that includes said receiver axis and said plurality of implantation axes, said movement of said seat member aligning said support surface with any of said plurality of implantation axes; and
a securing member engageable to said receiver member to secure said connecting element in said receiver member.

14. The system of claim 13, wherein:
said support surface of said seat member includes a length and said connecting element extends along said length;
said support surface is concavely curved transversely to said length to extend at least partially around said connecting element; and
said support surface is linear along said length.

15. The system of claim 13, wherein said seat member includes:
a distally opening socket portion configured to pivotally receive said anchor member in said receiver member.

16. The system of claim 13, wherein said seat member includes a through-hole extending through said support surface and into said socket portion.

17. The system of claim 13, wherein said socket portion includes a concavely curved inner surface and a convexly curved outer surface extending around said socket portion.

18. A system for stabilizing a bony segment, comprising:
a coupling assembly engageable to an elongate connecting element, wherein said coupling assembly comprises:
an anchor member engageable to the bony segment;
a receiver member coupled to said anchor member and extending proximally from said anchor member, said receiver member including a pair of arms extending proximally along a receiver axis centrally located between said arms, said arms further defining a passage for receiving the elongate connecting element along any one of a plurality of implantation axes that are transverse to said receiver axis;
a seat member positioned in said receiver member proximally of said anchor member, said seat member including a proximal saddle portion having a support surface, wherein said seat member is received in movable engagement with said receiver member with movement of said seat member limited to a plane including said receiver axis and said plurality of implantation axes to align said support surface with any of said implantation axes; and
a securing member engageable to said receiver member proximally of said anchor member;
wherein said proximal saddle portion has opposite proximally projecting ears and opposite flats on an outer surface of said saddle portion extending along said ears, said flats contacting an inner surface of said receiver member to limit said movement of said seat member to said plane.

19. The system of claim 18, wherein said support surface includes a length extending along an aligned one of said implantation axes, wherein said support surface is concavely curved transversely to said length and linear along said length.

20. The system of claim 18, wherein said seat member includes:
a distally opening socket portion configured to pivotally receive said anchor member in said receiver member.

21. The system of claim 18, wherein said socket portion includes a concavely curved inner surface and a convexly curved outer surface extending around said socket portion.

22. The system of claim 18, wherein said support surface is planar.

* * * * *